(12) United States Patent
Lim et al.

(10) Patent No.: US 8,871,470 B2
(45) Date of Patent: Oct. 28, 2014

(54) ADAPTIVE THERMAL BLOCK TEMPERATURE CONTROL METHOD AND SYSTEM

(75) Inventors: Chee Kiong Lim, Singapore (SG); Chee Wee Ching, Malaysia (MY)

(73) Assignee: Applied Biosystems, LLC, Carlsbad, CA (US)

( * ) Notice: Subject to any disclaimer, the term of this patent is extended or adjusted under 35 U.S.C. 154(b) by 934 days.

(21) Appl. No.: 12/053,416

(22) Filed: Mar. 21, 2008

(65) Prior Publication Data

US 2008/0248534 A1    Oct. 9, 2008

Related U.S. Application Data

(60) Provisional application No. 60/896,087, filed on Mar. 21, 2007.

(51) Int. Cl.
  *C12P 19/34* (2006.01)
  *G05D 23/32* (2006.01)
  *B01L 7/00* (2006.01)

(52) U.S. Cl.
  CPC ........... *B01L 7/52* (2013.01); *B01L 2300/1827* (2013.01); *G05D 23/32* (2013.01); *B01L 2200/147* (2013.01)
  USPC ...................................................... 435/91.2

(58) Field of Classification Search
  USPC ......................................... 435/91.2; 700/269
  See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,889,818 A | 12/1989 | Gelfand et al. | |
| 5,475,610 A | 12/1995 | Atwood et al. | |
| 7,133,726 B1 | 11/2006 | Atwood et al. | |
| 7,188,001 B2 | 3/2007 | Young et al. | |
| 2006/0286659 A1 | 12/2006 | Atwood et al. | |

FOREIGN PATENT DOCUMENTS

EP           0258017        3/1988

OTHER PUBLICATIONS

International Search Report for application No. PCT/US08/57907 dated Jun. 25, 2008, along with Written Opinion of the International Searching Authority.
PCTUS08057907, "Written Opinion of the Intl Searching Authority mailed Jun. 25, 2008", 4 pgs.
International Application No. PCT/US2808/057907, International Preliminary Report on Patentability mailed Oct. 1, 2009, 6 pages.

*Primary Examiner* — Cynthia B Wilder

(57) ABSTRACT

Aspects of the present teachings describe a method and apparatus for automatically controlling a block temperature to reduce undershooting and overshooting of the temperatures of a sample contained in the block and participating in a polymerase chain reaction (PCR). The adaptive thermal block temperature control begins when a sample temperature enters a sample window region between a preliminary setpoint temperature and a target setpoint temperature for the sample. Based on thermodynamic behavior of the sample and the predetermined phase of PCR, predicting a time period measured subsequent to the preliminary setpoint temperature when the sample will reach the target setpoint suitable for the predetermined phase of PCR. During this time period, varying the block temperature ramp rate with a series of cooling and heating changes to ensure the block temperature reaches the target setpoint temperature at approximately the same time as the sample reaches the same. Synchronizing the block temperature and sample temperature to the target setpoint temperature reduces undershooting and overshooting of the sample temperature and increases the speed and efficiency of the overall PCR process as it relates to the thermal cycling operations.

3 Claims, 6 Drawing Sheets

ADAPTIVE THERMAL BLOCK TEMPERATURE CONTROL METHOD AND SYSTEM

CROSS-REFERENCE TO RELATED APPLICATIONS

This application is related to and has an effective filing date of Provisional Application No. 60/896,087 filed Mar. 21, 2007 assigned to the assignee of the present invention entitled, "Adaptive Thermal Block Temperature Control Method and System" by Chee Kiong LIM and Chee Wee CHING which is incorporated herein by reference.

FIELD

The present teachings relate to the field of instruments for performing polymerase chain reaction. More particularly, the present teachings pertain to systems and methods for temperature control in instruments capable of performing polymerase chain reaction

INTRODUCTION

Polymerase Chain Reaction (PCR) has proven a phenomenally successful technology for genetic analysis. A key aspect of PCR is the concept of thermocycling: alternating steps of melting a nucleic acid template, annealing primers to the resulting single strands, and extending those primers to make new copies of double stranded nucleic acid. In thermocycling, a PCR reaction mixture may be repeatedly cycled from high temperatures for melting the DNA, to lower temperatures for primer annealing and extension.

In a typical PCR reaction, the reaction mixture is desirably transitioned and maintained accurately at various temperatures for prescribed time periods with temperature cycling frequently repeated many times. Generally, it is desirable to change the sample temperature to the next temperature in the cycle rapidly for several reasons. First, the chemical reaction may have an optimum temperature for each of its stages. Thus, less time spent at nonoptimum temperatures may improve the result product. Another reason is that a minimum time for holding the reaction mixture at each incubation temperature may be desired after each incubation temperature is reached. These minimum incubation times may establish "floor" or minimum time it takes to complete a cycle. Any time transitioning between sample incubation temperatures is time which is added to this minimum cycle time. Since the number of cycles is often fairly large, this additional time lengthens the total time needed to complete the amplification. Another important consideration is achieving each desired sample temperature with minimal under and/or overshooting which may adversely affect the resultant product or increase the overall reaction time.

BRIEF DESCRIPTION OF THE DRAWINGS

The skilled artisan will understand that the drawings, described below, are for illustration purposes only. The drawings are not intended to limit the scope of the present teachings in any way.

SUMMARY

Figure 1:
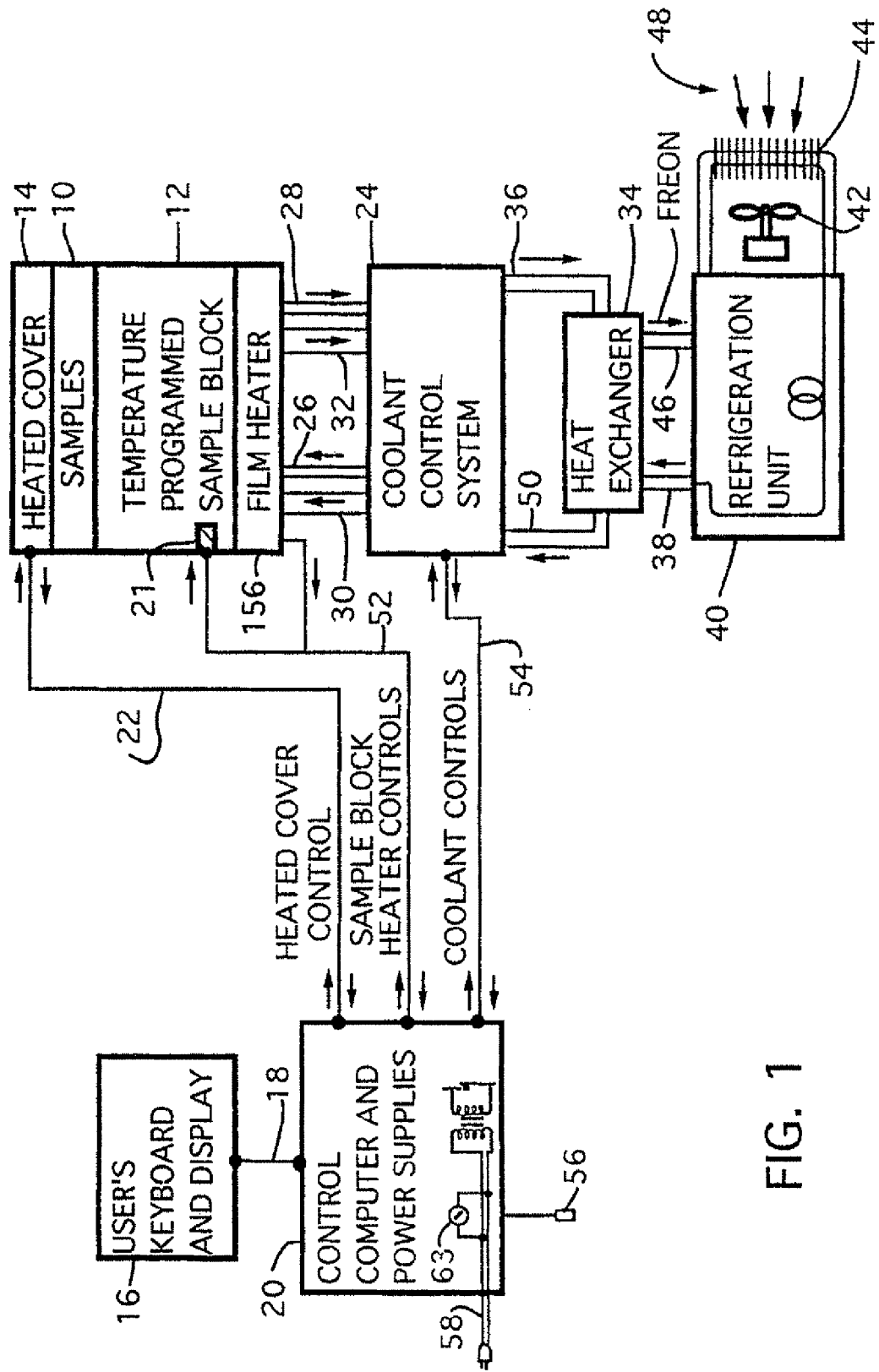
FIG. 1 is a schematic illustrating a block diagram of the major system components of one embodiment of a computer directed instrument for performing PCR in accordance with various implementations of the present teachings.

In various embodiments the present teachings describe a computer implemented method of controlling a thermal cycler for use in PCR. The method further comprising: determining a current temperature ramp rate for a sample being processed in a thermal block; predicting an expected time interval for the sample to reach a target setpoint temperature based upon the current temperature ramp rate for the sample; operating the thermal block at a target block ramp rate according to the predicted time interval for the sample to reach the target setpoint temperature; repeating determination of the current temperature ramp rate for the sample as the thermal protocol for PCR is performed in real-time; determining whether the predicted time interval for sample to reach target setpoint temperature has changed based on the current temperature ramp rate; and modifying the predicted time interval and the target block ramp rate to ensure target block and sample both reach target setpoint temperature at approximately same time.

In another embodiment the present teachings describe an apparatus for controlled automated performance of polymerase chain reactions. The apparatus further comprising: at least one sample comprising a PCR mixture to be amplified and contained in a sample vessel whose temperature is varied by association with a thermal block of variable temperature; and a control module implementing a PCR thermal protocol configured to vary the temperature of the thermal block and further configured to perform the steps of: determining a current temperature ramp rate for the sample; predicting an expected time interval for the sample to reach a target setpoint temperature based upon the current temperature ramp rate for the sample; operating the thermal block at a thermal block ramp rate according to the predicted time interval for the sample to reach the target setpoint temperature; repeating determination of the current temperature ramp rate for the sample as the thermal protocol for PCR is performed; determining whether the predicted time interval for sample to reach target setpoint temperature has changed based on the current temperature ramp rate; and modifying the predicted time interval and the thermal block ramp rate such that the thermal block and sample reach target setpoint temperature at approximately same time.

In yet other embodiments, the present teachings describe a method for polymerase chain reaction (PCR) temperature control. The method comprising the steps of; determining a current temperature ramp rate for a sample processed in a thermal block; predicting an expected time interval for the sample to reach a target setpoint temperature based upon the current temperature ramp rate for the sample; operating the thermal block at a target block ramp rate according to the predicted time interval for the sample to reach the target setpoint temperature; repeating determination of the current temperature ramp rate for the sample as the thermal protocol for PCR is performed; determining whether the predicted time interval for sample to reach target setpoint temperature has changed based on the current temperature ramp rate; and modifying the predicted time interval and the target block ramp rate to ensure target block and sample reach target setpoint temperature at approximately same time.

These and other features of the present teachings are set forth herein.

DESCRIPTION

The present teachings provide improved methods for temperature control in PCR processes. Details of the polymerase chain reaction process, the temperature cycling and reaction conditions used in PCR as well as the various reagents and enzymes used to perform the reaction are described in U.S. Pat. Nos. 4,683,202, 4,683,195, EPO Publication 258,017 and U.S. Pat. No. 4,889,818, which are hereby incorporated by reference. Details of instruments for use in PCR are described in U.S. Pat. Nos. 5,475,610 and 7,133,726 assigned to the assignee of the present invention and which are incorporated herein by reference.

In various PCR instruments, the reaction mixture may be stored or contained in a tube, well, through-hole or other fluid containment region provided by a substrate or vessel. A typical sample volume may be between approximately 10 nanoliters and 1000 microliters although greater or lesser amounts of reaction mixture may be readily amplified. Typically, such instruments may be configured to simultaneously amplify multiple sample reaction mixtures accomplished by heat transfer to and from all associated heat transfer block (for example, a metal or metal alloy sample block). In various embodiments, the PCR process is performed by controlling the temperature of the heat transfer block according to prescribed temperatures and times specified by the user in a PCR protocol file.

A computer and associated electronics controls the temperature of the heat transfer block in accordance with the user supplied data in the PCR protocol file defining the times, temperatures and number of cycles, etc. As the heat transfer block changes temperature, the samples follow with similar changes in temperature. However, one challenge in heating each sample is to maintain a consistent temperature between all samples while at the sample time raising and lowering sample temperatures accurately. Prior art PCR instruments typically possess a degree of error in sample temperatures generated by nonuniformity of temperature from place to place within the heat transfer block as well as suffering from a lack accuracy when raising and lowering the temperature of all samples in comparison to a desired temperature profile.

In one aspect, delays in transferring heat between the sample block and the sample creates deviations from desired temperature ramping profiles. To change the sample temperature to a setpoint level, the sample block is generally configured to exchange the appropriate amount of heat with the samples in the sample block. Allowing too much heat transfer from the sample block can cause a sample to either overshoot or undershoot the setpoint level depending on the temperature ramp rate for the sample and the sample block heat exchange characteristics.

Undershooting and/or overshooting temperatures may also introduce inaccuracies in a particular protocol. For example, if the sample temperature overshoots/undershoots the setpoint level then the particular PCR protocol may not perform as designed, amplify less efficiently or fail to work at all. To improve the PCR process and help aid in successful and efficient reaction amplification, it is desirable to bring the sample temperature to the various setpoint levels without overshooting/undershooting the sample temperature. This is particular important in performing "quantitative" PCR where time delays and temperature errors need to be minimized. Achieving this goal can be increasingly difficult when the size of the heat transfer block used to heat and cool the samples is relatively large. In one respect, the relatively large thermal mass of the block may present difficulties in transitioning the block temperature up and down in the operating range with great rapidity. Additionally, the block may be associated with various external devices such as manifolds for supply and withdrawal of cooling liquid, block support attachment points, peltier devices, heat sinks and associated other peripheral equipment which create the potential for temperature gradients to exist across the block which exceed tolerable limits.

Referring to FIG. 1 there is a block diagram of the major system components of one embodiment of a computer directed instrument for performing PCR according to the teachings of the present teachings. Sample mixtures including the DNA or RNA to be amplified are placed in the temperature-programmed sample block 12 and may be covered by heated cover 14.

A user supplies data defining time and temperature parameters of the desired PCR protocol via a terminal 16 including a keyboard and display. The keyboard and display are coupled via bus 18 to a control computer 20 (hereafter sometimes referred to as a central processing unit or CPU). This central processing unit 20 includes memory which stores the control program, data defining the desired PCR protocol and calibration constants. The control program causes the CPU 20 to control temperature cycling of the sample block 12 and implements a user interface which provides certain displays to the user and which receives data entered by the user via the keyboard of the terminal 16.

In one implementation, the central processing unit 20 is custom designed to facilitate improved performance and control over temperature cycling of the sample block 12. In alternative embodiments, the central processing unit 20 and associated peripheral electronics to control the various heaters and other electro-mechanical systems of the instrument and read various sensors could be any general purpose computer such as a suitably programmed personal computer or microcomputer.

The samples 10 are contained in vessels which are seated in or in proximity with the sample block 12 and may be thermally isolated from the ambient air by a heated cover 14. The heated cover 14 may serve, among other things, to reduce undesired heat transfers to and from the sample mixture by evaporation, condensation and refluxing inside the sample tubes. It may also reduce the chance of cross contamination by keeping the insides of the caps dry thereby preventing aerosol formation when the tubes are uncapped.

The central processing unit 20 may include appropriate electronics to sense the temperature of the heated cover 14 and control electric resistance heaters therein to maintain the cover 14 at a predetermined temperature. Sensing of the temperature of the heated cover 14 and control of the resistance heaters therein may be accomplished via a temperature sensor (not shown) and bus 22.

In one exemplary embodiment a coolant control system 24 continuously circulates a chilled liquid coolant through bias cooling channels (not shown) in the sample block 12 via input tubes 26 and output tube 28. The coolant control system 24 also controls fluid flow through higher volume ramp cooling fluid flow paths (not shown) in the sample block 12. The ramp cooling channels are used to rapidly change the temperature of the sample block 12 by pumping large volumes of chilled liquid coolant through the block at a relatively high flow rate. Ramp cooling liquid coolant enters the sample block 12 through tube 30 and exits the sample block through tube 32.

The liquid coolant used to chill the sample block 12 may comprise a mixture of water and ethylene glycol. The liquid coolant may be chilled by a heat exchanger 34 that receives liquid coolant with heat extracted from the sample block 12 via input tube 36. The heat exchanger 34 receives compressed liquid Freon refrigerant via input tube 38 from a refrigeration unit 40. This refrigeration unit 40 includes a compressor (not shown), a fan 42 and a fin tube heat radiator 44. The refrigeration unit 40 compresses Freon gas received from the heat exchanger 34 via tube 46. The gaseous Freon is cooled and condensed to a liquid in the fin tube condenser 44. The pressure of the liquid Freon is maintained above its vapor pressure in the fin tube condenser 44 by a flow restrictor capillary tube 47. The output of this capillary tube 47 is coupled to the input of the heat exchanger 34 via input tube 38. In the heat exchanger 34, the pressure of the Freon is allowed to drop below the Freon vapor pressure, and the Freon expands.

During the expansion process, heat is absorbed from the warmed liquid coolant circulating in the heat exchanger 34 and this heat is transferred to the Freon thereby causing the Freon to boil. The warmed Freon is then extracted from the heat exchanger 34 via tube 46 and is compressed and again circulated through the fin tube condenser 44. The fan 42 blows air through the fin tube condenser 44 to cause heat in the freon from tube 46 to be exchanged with the ambient air. As symbolized by arrows 48. In one embodiment, the refrigeration unit 40 should be capable of extracting 400 watts of heat at 30.degree C. and 100 watts of heat at 10 degree C. from the liquid coolant to support the rapid temperature cycling as needed in various aspects of the present teachings.

After exchanging its heat with the Freon, the liquid coolant exits the heat exchanger 34 via tube 50 and reenters the coolant control system where it is gated as needed to the sample block during rapid cooling portions of the PCR cycle defined by data entered by the user via terminal 16.

An alternative sample heating apparatus may include a Peltier based thermoelectric device such as those described in commonly assigned U.S. Pat. No. 7,133,726. Heat-pumping into and out of the samples is accomplished by using a Peltier thermoelectric component that may be constructed of pellets of n-type and p-type bismuth telluride connected alternately in series. The interconnections between the pellets may be made with copper which is bonded to a substrate, usually a ceramic (typically alumina).

Figures 2, 2A:
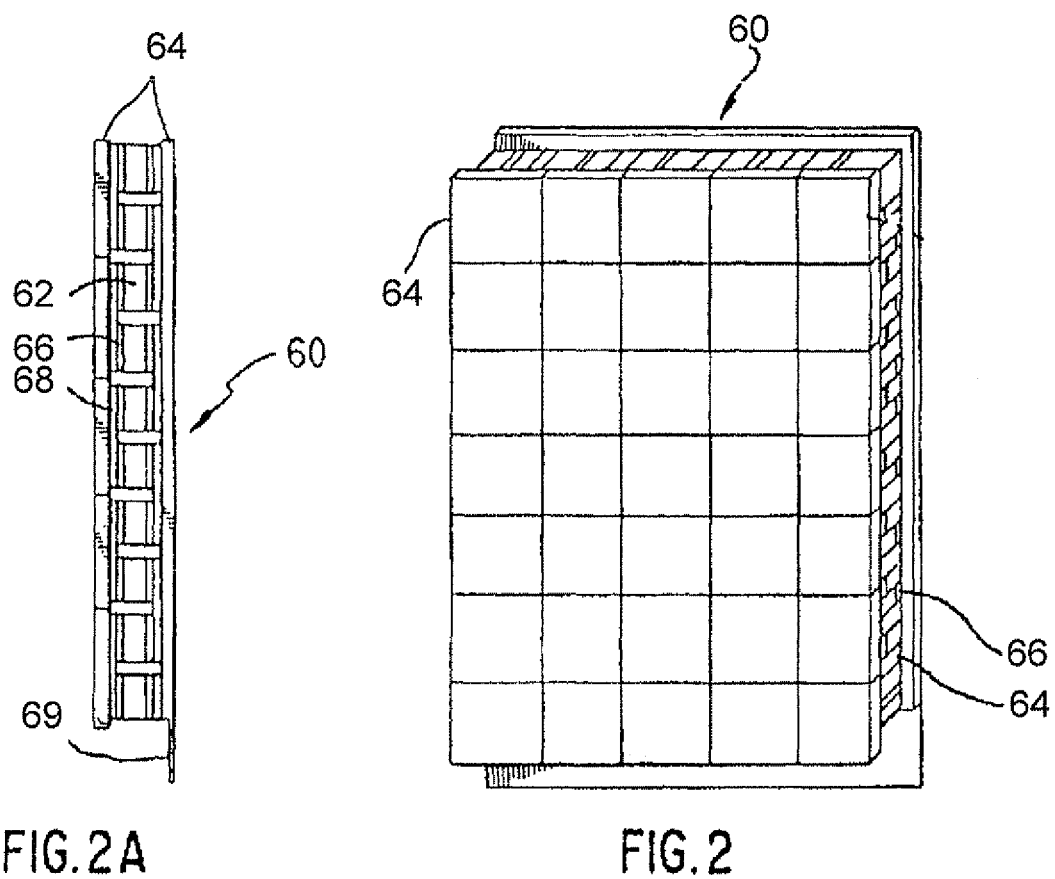
FIG. 2 is a schematic illustrating an alternative peltier-based thermocycler component in accordance with various implementations of the present teachings.
FIG. 2A is a schematic illustrating another view of the alternative peltier-based thermocycler component in accordance with various implementations of the present teachings.

The amount of heat-pumping desired is dependent on the thermal load and the ramp rate, that is, the rate at which the temperature is required to change. Factors such as the composition and configuration of the sample block, thermoelectric devices, heatsink, fan and the thermal interface media between the thermoelectric devices and both the heatsink and the sample block may also affect the heat-pumping parameters. In these devices samples may be heated by an apparatus depicted in FIGS. 2 and 2A reflecting a typical Peltier thermal electric device 60. The device is composed of bismuth telluride pellets 62, sandwiched between two alumna layers 64. The pellets are electrically connected by solder joints 66 to copper traces 68 plated onto the alumina layers. One alumina layer has an extension 69 to facilitate electrical connections. The thickness of the extended areas may be reduced to decrease the thermal load of the device.

Generally PCR reaction temperatures occur above ambient for example in the range 30 to 104° C. In the most cases the block is heated or cooled between at least two above ambient temperatures where the flow of heat due to conduction is from the block to the heat sink. In one aspect, system cycle time may be optimized for a given block configuration to achieve a desired balance between the boost to the ramp rate when cooling provided by the conduction, against the boost provided to the heating ramp rate by the Joule effect of resistance heating.

Figure 3A:
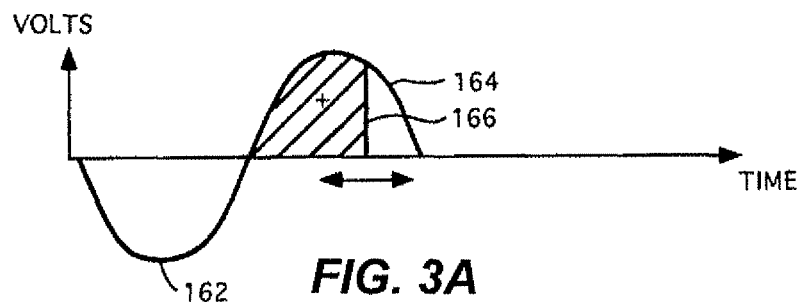
FIG. 3A is a schematic illustrating one embodiment of a power control concept for a film heater in accordance with various implementations of the present teachings.
Figure 3B:
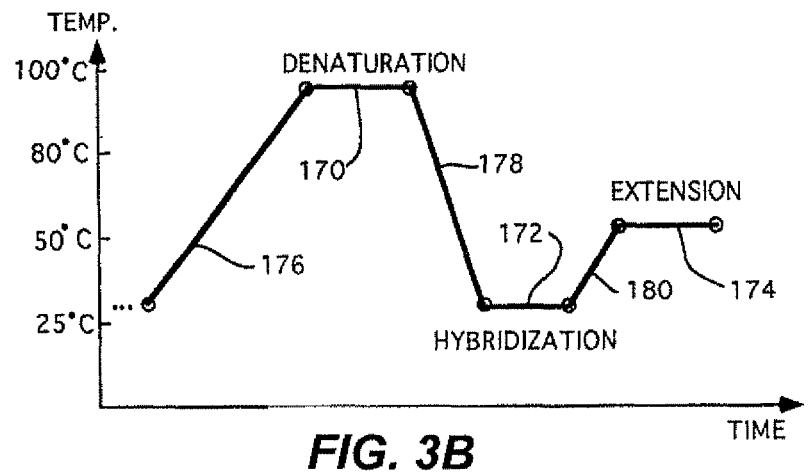
FIG. 3B is a schematic illustrating a time versus temperature plot of a typical PCR protocol.

FIG. 3B exemplifies a typical PCR cycle with a denaturation incubation 170 done at a temperature near 94 degree C., a hybridization incubation 172 done at a temperature near room temperature (25 degree C. to 37 degree C.) and an extension incubation 174 done at a temperature near 50 degree C. These temperatures are substantially different, and, therefore it is desirable to have equipment and methods of moving the temperature of the reaction mixture of all the samples rapidly from one temperature to another.

In operation using the exemplary thermalcycler configuration shown in FIG. 1, CPU 20 controls multi-zone heater 156 via bus 52. The temperature of multi-zone heater 156 can be controlled to raise the temperature of the sample block 12 rapidly to higher incubation temperatures from lower incubation temperatures. It is also capable of compensating for bias cooling and correcting temperature errors in the upward direction during temperature tracking and during incubations. In alternative embodiments, bias cooling may be eliminated or may be supplied by other means such as by the use of a cooling fan and cooling fins formed in the metal of the sample block, peltier junctions or constantly circulating tap water.

For the liquid cooled apparatuses CPU 20 controls the temperature of the sample block 12 by sensing the temperature of the metal of the sample block via temperature sensor 21 and bus 52 in FIG. 1 and by sensing the temperature of the circulating coolant liquid via bus 54 and a temperature sensor in the coolant control system. The CPU also senses the internal ambient air temperature within the housing of the system via an ambient air temperature sensor 56 in FIG. 1. Further, the CPU 20 senses the line voltage for the input power on line 58 via a sensor symbolized at 63.

A control program uses these items of data together with items of data entered by the user to define the desired PCR protocol such as target temperatures and times for incubations. This control program calculates the amount of power to apply to the various zones of the multi-zone sample block film heater 156 via the bus 52 and generates a coolant control signal to open or close the solenoid operated valve 55 in the coolant control system 24 via bus 54 causing the temperature of the sample block to follow the PCR protocol defined by data entered by the user. As will be appreciated by one of skill in the art, the temperature control provided by the CPU 20 may be adapted for use with other heating/cooling configurations such as solid state/peltier-based systems or other components which heat and cool the sample block to achieve the desired temperature profiles for sample thermocycling.

Irrespective of the manner in which the sample is heated and cooled, it is particularly important to perform PCR amplification with a high degree of temperature control and precision. Accordingly, it is important to maintain precise control over sample mixture temperature as between various ones of a multiplicity of different samples. For example, if all the samples are not precisely controlled to have the proper annealing temperature for the extension incubation certain forms of DNA may not extend properly. This happens because the primers used in the extension process may anneal to the wrong DNA template if the temperature is too low. If the annealing temperature is too high, the primers may not anneal to the target DNA at all.

FIG. 3A illustrates one exemplary embodiment of a power control concept that may be used in connection with the film heater 156, peltier-based thermal transfer approach and other thermocycler designs or configurations. FIG. 3A diagrams an exemplary voltage waveform for a supply line voltage. Rectification to eliminate the negative half cycle 162 may occur and in certain embodiments only positive half cycles may remain of which half cycle 164 is typical. The CPU 20 and its associated peripheral electronic circuitry may then control the portion of each half cycle which is applied to the various zones of the film heater 156 by selecting a portion of each half cycle to apply according to a power level computed for each zone based upon equations given below for each zone. That is, the dividing line 166 is moved forward or backward along the time axis to control the amount of power to the film heater based upon a number of factors which are related in a special equation for each zone. The cross-hatched area under the positive half cycle 164 represents the amount of power applied to the film heater 156 for the illustrated position of the dividing line 166. As the dividing line 166 is moved to the right, more power is applied to the film heater, and the sample block 12 gets hotter. As the dividing line is moved to the left along the time axis, the cross-hatched area becomes smaller and less power is applied to the film heater.

Referring to FIG. 3B, there is shown a time versus temperature plot of a typical PCR protocol. Large downward changes in block temperature are accomplished by cooling the sample block while monitoring the sample block temperature by the temperature sensor 21 in FIG. 1. Typically these rapid downward temperature changes are carried out during the ramp following the denaturation incubation 170 to the temperature of hybridization incubation 172. Typically, the user must specify the protocol by defining the temperatures and times in one fashion or another so as to describe to the CPU 20 the positions on the temperature/time plane of the checkpoints symbolized by the circled intersections between the ramp legs and the incubation legs. Generally, the incubation legs are marked with reference numerals 170, 172 and 174 and the ramps are marked with reference numerals 176, 178 and 180.

Generally the incubation intervals are conducted at a single temperature, but in alternative embodiments, they may be stepped or continuously ramped to different temperatures within a range of temperatures which is acceptable for performing the particular portion of the PCR cycle involved. That is, the denaturation incubation 170 need not be carried out at one temperature as shown in FIG. 3B, but may be carried out at any of a plurality of different temperatures within the range of temperatures acceptable for denaturation. In some embodiments, the user may specify the length of the ramp segments 176, 178 and 180. In other embodiments, the user may only specify the temperature or temperatures and duration of each incubation interval, and the instrument will then move the temperature of the sample block as rapidly as possible between incubation temperatures upon the completion of one incubation and the start of another. In the preferred embodiment, the user can also have temperatures and/or incubation times which are different for each cycle or which automatically increment on every cycle.

In one exemplary embodiment, the amount heat added to or removed is estimated from the block, the CPU 20 measures the block temperature using temperature sensor 21 in FIG. 1 and measures the coolant temperature by way of temperature sensor coupled to bus 54 in FIG. 1. In addition, CPU 20 uses additional sensors to measure ambient air temperature and the power line voltage, which controls the power applied to the film heaters on bus 52. The thermal conductance from the sample block to ambient air and from the sample block to the coolant are known to the CPU 20 as a result of measurements made during an initialization process to set control parameters of the system.

For good temperature uniformity of the sample population, the block, at constant temperature, should have little or no net heat flow in or out. However, temperature gradients can occur within the sample block arising from local flows of heat from hot spots to cold spots which have zero net heat transfer relative to the block borders. For instance, a slab of material which is heated at one end and cooled at the other is at a constant average temperature if the net heat flow into the block is zero. However, in this situation a significant temperature nonuniformity, e.g., a temperature gradient, can be established within the slab due to the flow of heat from the hot edge to the cold edge. When heating and cooling of the edges of the block are stopped, the flow of heat from the hot edge to the cold edge eventually dissipates this temperature gradient and the block reaches a uniform temperature throughout which is the average between the hot temperature and cool temperature at the beginning of heat flow.

Practically speaking, it is not always practical to control the temperature of a sample block without some heat flow in and out. The cold bias control cooling requires some heat flow in from the strip heaters to balance the heat removed by the coolant flowing through the bias cooling channels to maintain the block temperature at a stable value. The key to a uniform sample block temperature under these conditions is a geometry which has "local balance" and "local symmetry" of heat sources and heat sinks both statically and dynamically, and which is arranged such that any heat flow from hot spots to cold spots occurs only over a short distance.

Stated briefly, the concept of "static local balance" means that in a block at constant temperature where the total heat input equals the total heat output, the heat sources and heat sinks are arranged such that within a distinct local region, all heat sources are completely balanced by heat sinks in terms of heat flows in and heat flows out of the block. Therefore, each local region, if isolated, would be maintained at a constant temperature.

The concept of "static local symmetry" means that, within a local region and for a constant temperature, the center of mass of heat sources is coincident with the center of mass of heat sinks. If this were not the case, within each local region, a temperature gradient across each local region can exist which can add to a temperature gradient in an adjacent local region thereby causing a gradient across the sample block which is twice as large as the size of a single local region because of lack of local symmetry even though local balance within each local region exists. The concepts of local balance and local symmetry are important to the achievement of a static temperature balance where the temperature of the sample block is being maintained at a constant level during, for example, an incubation interval.

For the dynamic case where rapid temperature changes in the sample block are occurring, the thermal mass, or heat capacity of each local region becomes important. This is because the amount of heat that must flow into each local region to change its temperature is proportional to the thermal mass of that region.

Therefore, the concept of static local balance can be expanded to the dynamic case by requiring that if a local region includes x percent of the total dynamic heat source and heat sink, it must also include x percent of the thermal mass for "dynamic local balance" to exist. Likewise, "dynamic local symmetry" requires that the center of mass of heat capacity be coincident with the center of mass of dynamic heat sources and sinks. What this means in simple terms is that the thermal mass of the sample block is the metal thereof, and the machining of the sample block must be symmetrical and balanced such that the total mass of metal within each local zone is the same. Further, the center of mass of the metal in each local zone should be coincident with the center of mass of the dynamic heat sources and sinks. Thus, the center of mass of the multi-zone heater 156, e.g., its geometric center, and the geometric center of the bias and ramp cooling channels must coincide.

Figure 3C:
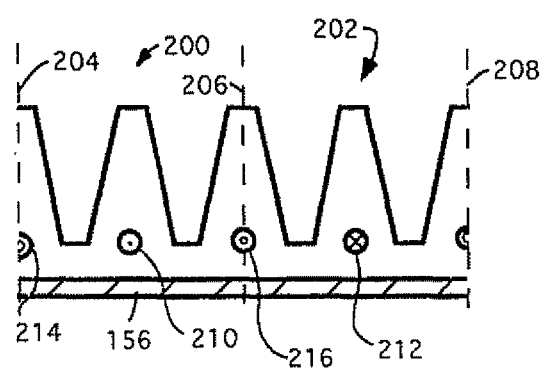
FIG. 3C illustrates two local regions side by side for a design of a sample block in accordance with aspects of the present teachings.

FIG. 3C illustrates two local regions side by side for the design of the sample block 12 in accordance with aspects of the present teachings. In FIG. 3C, the boundaries of two local regions, 200 and 202, are marked by dashed lines 204, 206 and 208. FIG. 3C shows that each local region which is not in the guard band is comprised of: two columns of sample wells; a portion of the foil heater 156 which turns out to be ⅛th of the total area of the heater; one ramp cooling channel such as ramp cooling channels 210 and 212; and, one bias cooling channel. To preserve local symmetry, each local region is centered on its ramp cooling channel and has one-half of a bias cooling channel at each boundary.

For example, local region 200 has a center over the ramp cooling channel 210 and bias cooling channels 214 and 216 are dissected by the local region boundaries 204 and 206, respectively. Thus the center of mass of the ramp cooling channel (the middle thereof), coincides (horizontally) with the center of mass of the bias cooling channels (the center of the local region) and with the center of mass of the film heater portion coupled to each local region. Static local balance will exist in each local region when the CPU 20 is driving the film heater 156 to input an amount of heat energy that is equal to the amount of heat energy that is being removed by the ramp cooling and bias cooling channels.

Dynamic local balance for each local region exists because each local region in the center portion of the block where the 96 sample mixtures reside contains approximately ⅛th the total thermal mass of the entire sample block, contains ⅛th of the total number of ramp cooling channels and contains ⅛th of the total number of bias cooling channels. Dynamic local symmetry exists for each local region, because the center of mass of the metal of each local region is horizontally coincident with the center of film heater portion underlying the local region; the center of the ramp cooling channel; and, the center of mass of the two half bias cooling channels. By virtue of these physical properties characterized as static and dynamic local balance and local symmetry, the sample block heats and cools all samples in the population uniformly.

Figure 4:
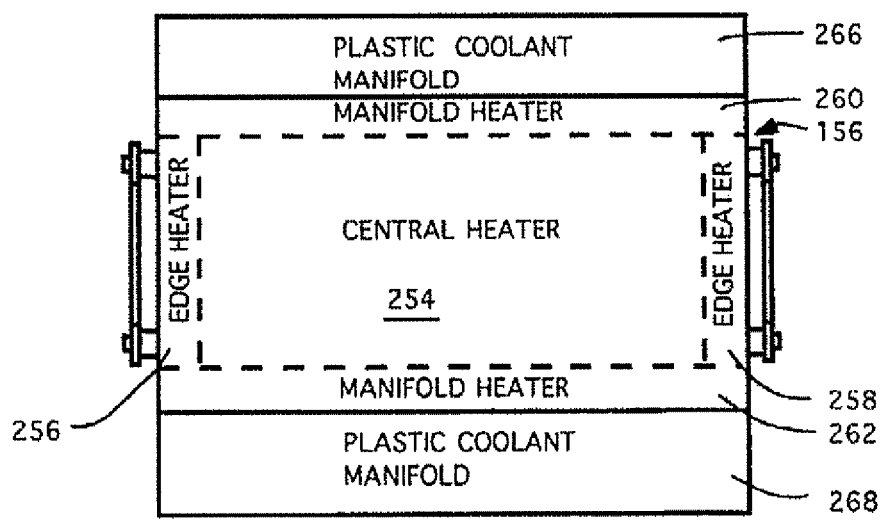
FIG. 4 is a schematic illustrating three separately controlled zones within a film heater layer in accordance with various implementations of the present teachings.

Referring to FIG. 4A, there are shown three separately controlled zones within the film heater layer 156. These separately controlled zones include edge heater zones which are situated under the guard bands at the exposed edges of the sample block 12 which are coupled to the support bracket 148. There are also separately controlled manifold heater zones situated under the guard bands for the edges 228 and 230 which are attached to the coolant manifolds. Finally, there is a central heater zone that underlies the sample wells. The power applied to each of these zones is separately controlled by the CPU 20 and the control software.

The film heater 156 is composed of a pattern of electrical conductors formed by etching a thin sheet of metal alloy such as Inconel™. The metal alloy selected should have high electrical resistance and good resistance to heat. The pattern of conductors so etched is bonded between thin sheets of an electrically insulating polymeric material such as Kapton™. Whatever material is used to insulate the electrical resistance heating element, the material must be resistant to high temperatures, have a high dielectric strength and good mechanical stability.

The central zone 254 of the film heater has approximately the same dimensions as the central portion of the sample block inside the guard bands. Central region 254 delivers a uniform power density to the sample well area. Edge heater regions 256 and 258 are about as wide as the edge guard bands but are not quite as long. Manifold heater regions 260 and 262 underlie the guard bands for edges.

The manifold heater zones 260 and 262 are electrically connected together to form one separately controllable heater zone. In addition, the edge heater sections 256 and 258 are electrically coupled together to form a second separately controllable heater zone. The third separately controllable heater zone is the central section 254. Each of these three separately controllable heater zones has separate electrical leads, and each zone is controlled by a separate control algorithm which may be run on separate microprocessors or a shared CPU as is done in various embodiments.

The edge heater zones 256 and 258 are driven to compensate for heat lost to the support brackets. This heat loss is proportional to the temperature difference between the sample block 12 and the ambient air surrounding it. The edge heater zones 256 and 258 also compensate for the excess loss of heat from the sample block to the full bias cooling channels at each edge of the block. This heat loss is proportional to the temperature difference between the sample block 12 and the coolant flowing through these bias cooling channels.

The manifold heater sections 260 and 262 are also driven so as to compensate for heat lost to the plastic coolant manifolds 266 and 268 in FIG. 4A which are attached to the edges of the sample block 12. The power for the manifold heater sections 260 and 262 compensates for heat loss which is proportional mainly to the temperature difference between the sample block and the coolant, and to a lesser degree, between the sample block and the ambient air.

The control algorithm run by CPU 20 of FIG. 1 senses the temperature of the sample block via temperature sensor 21 in FIG. 1 and FIG. 9 and bus 52 in FIG. 1. This temperature is differentiated to derive the rate of change of temperature of the sample block 12. The CPU then measures the temperature of the ambient air via temperature sensor 56 in FIG. 1 and measures the temperature of the coolant a the temperature sensor in the coolant control system 24. The CPU 20 then computes the power factor corresponding to the particular segment of the PCR protocol being implemented and makes calculations for the power factor where the power factor is the total power needed to move the block temperature from its current level to the temperature level specified by the user via a setpoint.

After the required power to be applied to each of the three zones of the heater 156 is calculated, another calculation is made regarding the proportion of each half cycle of input power which is to be applied to each zone in some embodiments. In one embodiment described below, the calculation mode is how many half cycles of the total number of half cycles which occur during a 200 millisecond sample period are to be applied to each zone. In the alternative embodiment symbolized by FIG. 3A, the computer calculates for each zone, the position of the dividing line 166 in FIG. 3A. After this calculation is performed, appropriate control signals are generated to cause the power supplies for the multi-zone heater 156 to do the appropriate switching to cause the calculated amount of power for each zone to be applied thereto.

In alternative embodiments, the multi-zone heater can be implemented using a single film heater which delivers uniform power density to the entire sample block, plus one or two additional film heaters with only one zone apiece for the guard bands. These additional heaters are superimposed over the single film heater that covers the entire sample block. In such an embodiment, only the power necessary to make up the guard band losses is delivered to the additional heater zones.

The foregoing description illustrates how the sample block temperature may be controlled to be uniform and to be quickly changeable. However, in the PCR process, it is the temperature of the sample reaction mixture and not the block temperature that is to be programmed. In accordance with various embodiments of the present teachings, the user specifies a sequence of target temperatures for the sample liquid itself and specifies the incubation times for the sample liquid at each of these target temperatures for each stage in the PCR process. The CPU 20 then manages the sample block temperature so as to get the sample reaction mixtures to the specified target incubation temperatures and to hold the sample mixtures at these target temperatures for the specified incubation times. The user interface code run by the CPU 20 displays, at all stages of this process, the current calculated sample liquid temperature on the display of terminal 16.

The difficulty with displaying an actual measured sample temperature is that to physically measure the actual temperature of the reaction mixture requires insertion of a temperature measuring probe therein. The thermal mass of the probe can significantly alter the temperature of any well in which it is placed since the sample reaction mixture in any particular well is often only 100 microliters in volume. Thus, the mere insertion of a temperature probe into a reaction mixture can cause a temperature gradient to exist between that reaction mixture and neighboring mixtures. Since the extra thermal mass of the temperature sensor would cause the reaction mixture in which it is immersed to lag behind in temperature from the temperatures of the reaction mixtures in other wells that have less thermal mass, errors can result in the amplification simply by attempting to measure the temperature. Accordingly, the instrument described herein calculates the sample temperature from known factors such as the block temperature history and the thermal time constant of the system and displays this sample temperature on the display.

Figure 5A:
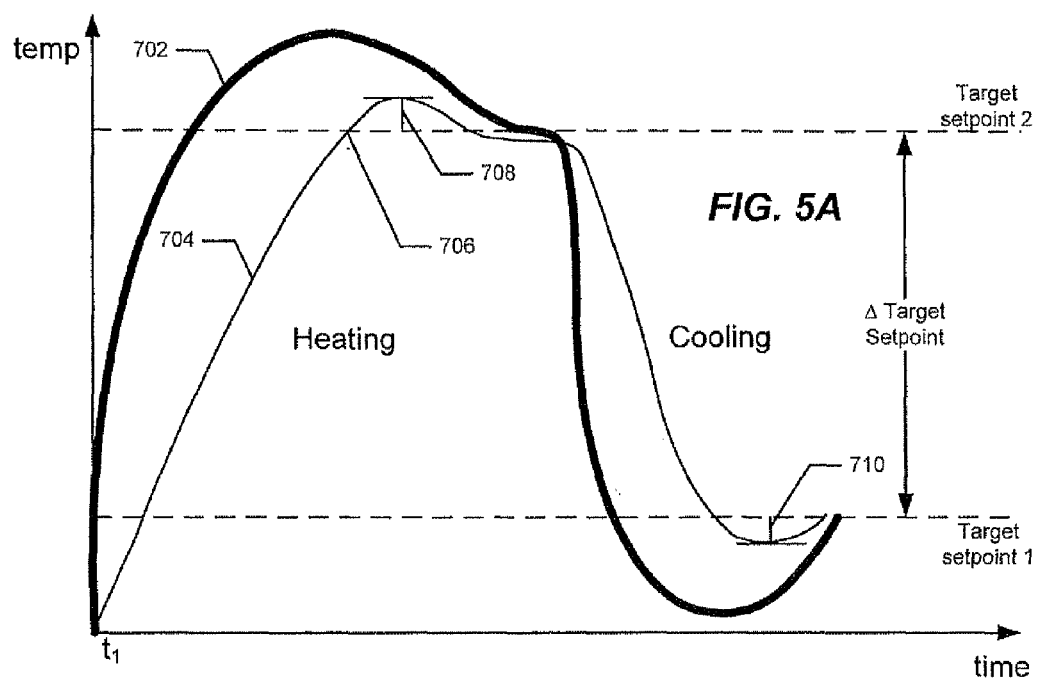
FIG. 5A is a schematic illustrating an example of operating a sample block at ramp rates that cause the sample temperature to either overshoot or undershoot setpoint targets.

FIG. 5A illustrates schematically an example of operating the sample block at ramp rates that cause the sample temperature to either overshoot or undershoot setpoint targets set in the thermal protocol. Typically, this occurs when the tuning parameters in the thermal protocol have not been optimized, improperly set, or have been applied to a different temperature range in the PCR process. For example, the tuning parameters suitable for denaturation incubation 170 in FIG. 3C may not incur sample temperature overshoot at this stage, however, when applied to hybridization incubation 172 portion of the PCR process these parameters may incur sample temperature undershoot. Indeed, FIG. 5A illustrates use of tuning parameters that incur both overshoot 708 and undershoot 710 of the sample temperature though in practice one or the other may occur independently and/or at various stages in the PCR protocol.

In practice, it may be desirable or acceptable for the block temperature 702 to be configured to overshoot the target setpoint temperature as long as the sample temperature does not do the same (or at least to a lesser degree). Rapid changes in block temperature 702 achieved with a high target block ramp rate may be used to urge the sample temperature to reach the target setpoint targets in a timely manner in accordance with the particular thermal protocol for PCR. Further, the block temperature 702 may be configured to overshoot/undershoot the target setpoint targets in order for the sample temperature 704 to reach target setpoint 1, target setpoint 2 or any other setpoint in the protocol in a more rapid manner without adverse effects on the sample amplification or reaction. In some cases, such overshooting/undershooting may be used to improve the thermal performance or rate of heating/cooling of the samples which may be most efficiently accomplished by reducing or minimizing sample overshoot/undershoot while permitting some degree of block temperature overshoot/undershoot.

In the illustrated example, the sample temperature 704 reaches target setpoint 2 during a heating cycle at time 706 but exceeds the specified temperature by overshoot amount 708 as the block temperature 702 has been sustained over a time period. In terms of the PCR process, the overshoot amount 708 may be undesirable or not deliver the requisite accuracy for the specified thermal protocol in relation to the sample temperature. This may her cause a reduction in sample amplification, loss of amplification fidelity, reduction in accuracy of the overall experiment, or a general failure of the PCR process. In some instances, it may also increase the overall processing time needed to complete a full PCR cycle.

Similarly as shown by way of example the block temperature 702 may operate to cool the sample temperature at a rapid rate to achieve target setpoint 1 in accordance with a user specified thermal protocol. Once again, the block temperature 702 may undershoot target setpoint 1 while transitioning the sample temperature to a desired level for hybridization incubation 172 per the PCR process. Instead of overshooting, the sample temperature 704 may instead undershoot the target setpoint 1 with respect to the specified thermal protocol and incur a similar set of resulting problems.

Figure 5B:
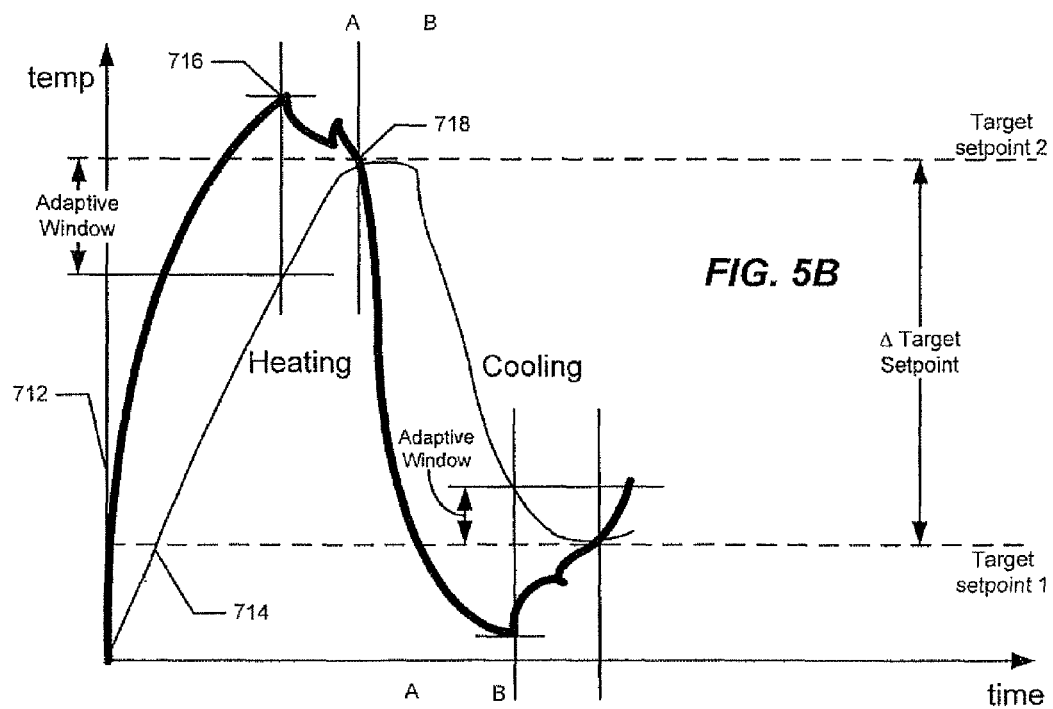
FIG. 5B is a schematic illustrating an example block temperature that operates with a rapid ramp rate to achieve a sample temperature timing specified in a thermal protocol

Aspects of the present teachings use an adaptive thermal block temperature control to minimize, reduce or potentially eliminate the sample temperature overshooting/undershooting of the target setpoints. As illustrated in FIG. 5B, a block temperature 712 operates with a rapid ramp rate to achieve the sample temperature 714 timing specified in the thermal protocol. CPU 20 uses a current block and sample temperature ramp rate to generate an expected sample time interval (B), as depicted in FIG. 5B, that it will take for the sample temperature to reach the target setpoint 2. CPU 20 also determines an synchronization time interval (A) offset from expected sample time interval (B) as determining the adaptive window. In one implementation, the synchronization time interval (A) may be tuned by a user based on consideration of the PCR process and the particular sample being amplified.

In various embodiments, the adaptive window defines a time period that the block temperature 712 is increased or decreased in order to reach the target setpoint at the same time as the sample temperature 714. Overshoot or undershoot is effectively reduced or eliminated as the block temperature 712 is at substantial equilibrium with the sample temperature 714 before entering the next portion of the PCR process. After entering the adaptive window in FIG. 5B, it can be seen that the block temperature may increased or decreased relatively in small amounts or as desired to help maintain the temperature gradient does not pull the sample temperature 714 into either an undesired overshoot or undershoot condition.

Figure 6:
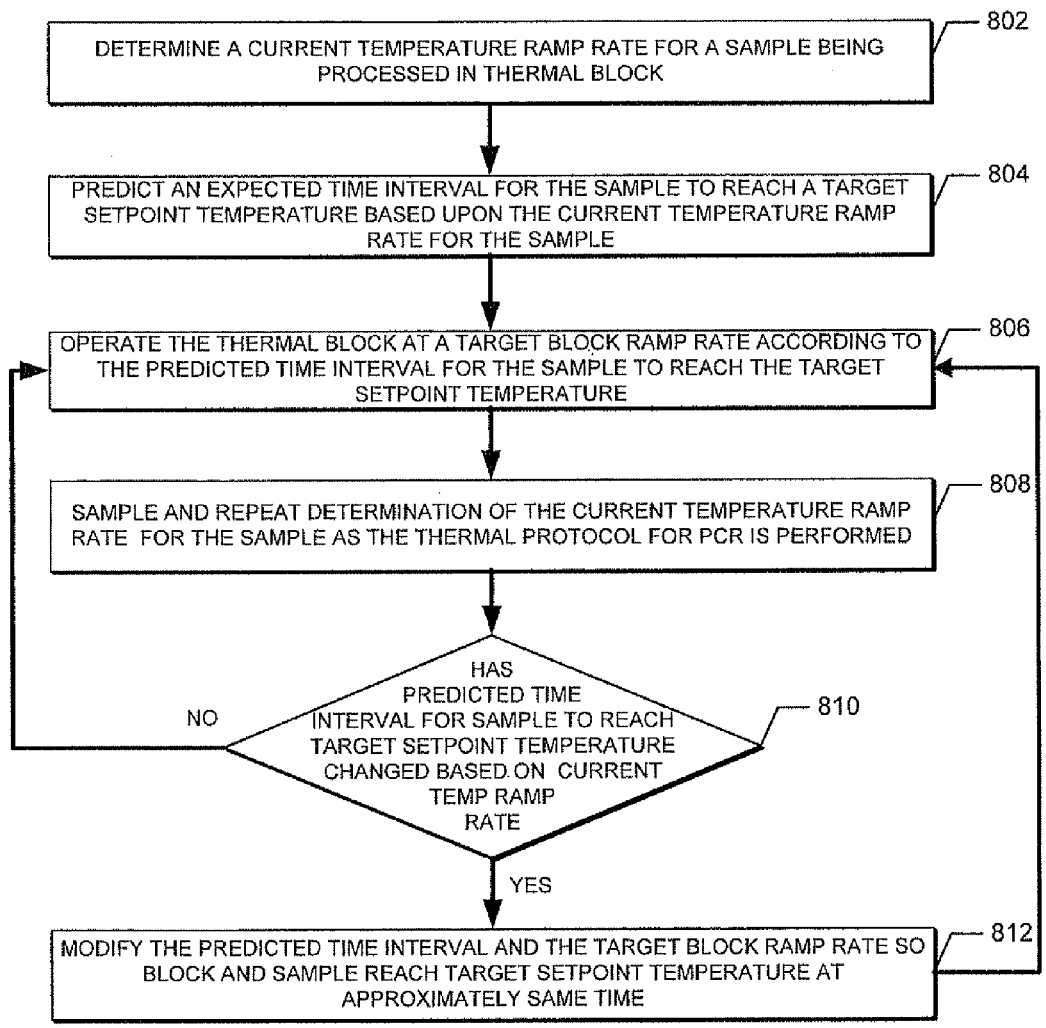
FIG. 6 is a flowchart diagram of the operations for performing an adaptive thermal block control in accordance with aspects of the present teachings.

FIG. 6 is a flowchart diagram of the operations for performing the adaptive thermal block control in accordance with aspects of the present teachings. One embodiment of the present teachings initially determines a current temperature ramp rate for a sample being processed in a thermal block (802). The sample temperature ramp rate may be determined empirically through various sensors in the system or may be set according to a variety of predetermined parameters.

Next, the current temperature ramp rate for the sample is used to predict an expected time interval that the sample will reach the target setpoint temperature (804). This expected time interval is typically based upon the current temperature ramp rate, sensor values returned by the system, parameter settings and other relevant values obtained during operation of the thermal cycler.

The thermal block holding the sample operates according to a block ramp rate and the predicted time interval for the target to reach the target setpoint temperature (806). In one implementation, the adaptive thermal block temperature control begins when the block temperature enters within the adaptive window previously described. Alternatively, the adaptive thermal block temperature control may begin sometime before the adaptive window if the block temperature behavior and sample temperature can be more accurately predicted and correlated together.

In one embodiment, sampling of the block temperature, sample temperature, ambient temperature and other measurements are made approximately 20 times per second. It will be appreciated, however, that sampling may occur with greater or lesser frequencies as configured or desired. In particular, aspects of the present teachings the sampling process repeats the determination of the current temperature ramp rate for the sample as the thermal protocol for PCR is performed in real-time (808).

The sample temperature ramp rate results are used to provide an improved degree of precision and control over the sample temperature through closer control of the block temperature. Aspects of the present teachings determine if the predicted time interval for the sample to reach the next target setpoint temperature has changed based on the measured temperature ramp rate (810). This information is useful for directing that the block temperature returns to the setpoint temperature at approximately the same time as the sample temperature. For example, if the sample temperature ramp rate has increased during heating then the block temperature may drop more rapidly to ensure the sample temperature does not substantially overshoot the setpoint. Similarly, if the sample temperature drops more quickly than expected or desired during a cooling region of the thermal protocol then the block temperature may be configured to increase more rapidly to avoid the sample temperature from reaching an undershooting condition.

Depending on change in the predicted time interval for the sample to reach the setpoint temperature, the block ramp rate may be increased or decreased for cooling or heating as desired. Accordingly, the predicted time interval and the target block ramp rate both or individually may be modified to maintain the block temperature and the sample temperature such that both reach the target setpoint temperature at approximately the same time (812). Such a control process is illustrated in FIG. 5B which depicts the result of applying the adaptive thermal block temperature control in accordance with aspects of the present teachings. As noted above, enhanced temperature control is achieved in both heating an cooling steps substantially avoiding both over-shooting and under-shooting of sample temperatures to improve PCR processes.

Having thus described various implementations and embodiments of the present teachings, it should be noted by those skilled in the art that the disclosures are exemplary only and that various other alternatives, adaptations and modifications may be made within the scope of the present teachings.

Embodiments of the present teachings can be implemented in digital electronic circuitry, or in computer hardware, firmware, software, or in combinations thereof. Apparatus of the present teachings can be implemented in a computer program product tangibly embodied in a machine-readable storage device for execution by a programmable processor; and method steps of the present teachings can be performed by a programmable processor executing a program of instructions to perform functions of the present teachings by operating on input data and generating output. The present teachings can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object-oriented programming language, or in assembly or machine language if desired; and in any case, the language can be a compiled or interpreted language. Suitable processors include, by way of example, both general and special purpose microprocessors. Generally, a processor will receive instructions and data from a read-only memory and/or a random access memory. Generally, a computer will include one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM disks. Any of the foregoing can be supplemented by, or incorporated in, ASICs.

Thus, the present teachings is not limited to the specific embodiments described and illustrated above. Instead, the present teachings is construed according to the claims that follow and the full scope of their equivalents thereof.

What is claimed is:

1. A method for polymerase chain reaction (PCR) temperature control, the method comprising the steps of:
   changing the temperature of a sample being processed in a thermal block between at least two target setpoint temperatures;
   calculating a sample temperature ramp rate at which the temperature of the sample is changing;
   calculating a time interval during which the temperature of the sample will reach the target setpoint temperature based upon the sample temperature ramp rate; and
   controlling the temperature of the thermal block to ensure both the thermal block and the sample reach the target setpoint temperature at essentially the same time within the calculated time interval.

2. The method of claim 1 wherein the expected time interval occurs during an adaptive window for adjusting the target block ramp rate.

3. The method of claim 2 wherein the adaptive window designates approximately where the sample is expected to reach the target setpoint temperature and wherein the target block ramp rate is modified so the sample and block both substantially reach the target setpoint temperature within the adaptive window.

\* \* \* \* \*